United States Patent [19]

Trumpower

[11] Patent Number: 4,832,754

[45] Date of Patent: May 23, 1989

[54] PROTEIN REMOVAL FROM SOFT CONTACT LENSES

[75] Inventor: Bernard L. Trumpower, Boston, Mass.

[73] Assignee: Dartmouth College, Hanover, N.H.

[21] Appl. No.: 8,744

[22] Filed: Jan. 30, 1987

Related U.S. Application Data

[63] Continuation-in-part of Ser. No. 606,942, May 4, 1984, abandoned.

[51] Int. Cl.[4] ............................................. B08B 3/10
[52] U.S. Cl. ...................................... 134/30; 134/42; 252/174.12; 252/DIG. 12
[58] Field of Search ............................. 134/30, 42; 252/DIG. 12, 174.12; 435/264; 422/28

[56] References Cited

U.S. PATENT DOCUMENTS

| | | | |
|---|---|---|---|
| 3,574,120 | 4/1971 | Siefert et al. | 252/135 X |
| 3,910,296 | 10/1975 | Karageozian et al. | 134/42 X |
| 4,104,187 | 8/1978 | Sibley et al. | 134/42 X |
| 4,285,738 | 8/1981 | Ogata | 134/42 X |
| 4,395,346 | 7/1983 | Kleist | 134/42 X |
| 4,521,254 | 6/1985 | Anderson et al. | 252/174.12 X |
| 4,609,493 | 9/1986 | Schäfer | 252/174.12 X |
| 4,614,549 | 9/1986 | Ogunbiyi et al. | 134/30 X |

FOREIGN PATENT DOCUMENTS 50-64303  5/1975  Japan ..................................... 134/42

*Primary Examiner*—Asok Pal
*Attorney, Agent, or Firm*—Rines and Rines

[57] ABSTRACT

A method is described for removing deposited protein from the surface of contact lenses during heat disinfection of the contact lenses using a heat stable protease.

10 Claims, 3 Drawing Sheets

PROTEIN REMOVAL FROM SOFT CONTACT LENSES

This is a continuation-in-part of application Ser. No. 606,942, filed May 4, 1984, now abandoned.

The present invention relates to a method of removing protein from the surface of contact lenses during heat disinfection using a heat stable protease.

Attention is called to U.S. Pat. Nos. 3,574,120 (Siebert); 3,910,296 (Karageozian et al.); 3,962,107 (Levin et al.); 4,011,169 (Barchert et al.); 4,021,377 (Barchert et al.); 4,065,324 (Rankin); 4,096,870 (Manfuso); 4,155,868 (Kaplan et al.); and 4,285,738 (Ogata).

Users of soft contact lenses, including the daily-wear lenses and the extended-wear lenses, must clean and disinfect their lenses for reasons of health and comfort. With daily-wear lenses this should be done on a daily basis. With extended-wear lenses this should be done every time the lenses are removed from the eye.

In addition to cleaning the soft lenses with detergent (e.g., Daily Cleaner, trademark for a detergent marketed by Bausch and Lomb), users must remove protein deposit from the surface of the soft lenses. The frequency with which protein deposit must be removed from the surface of the lenses varies with different individuals, and therefore, may be performed on a daily or a weekly basis. The presently used method (i.e., prior to the present invention) for removing protein deposit from the surface of soft contact lenses involves soaking the lenses in a protease for several hours at ambient temperature. This protease treatment is performed as a step separate from disinfection of the lenses.

Such proteases as are currently used for removing protein deposit are intended to be used at ambient temperature (25°–30° C.), at which temperature they are stable and active. Such proteases become progressively less active as the temperature is raised above 45° C., and would not be active at 78°–80° C., the temperature required for disinfection. Rather, at disinfecting temperatures, currently-used proteases would denature and deposit on the surface of the lenses, thus contributing to the problem which protease treatment is intended to solve, that is, protein deposit on the lens.

There are presently two methods used for disinfection of soft contact lenses. One method involves soaking the lenses in a solution of chemical disinfectant. This method is attractive because of its relative simplicity, but there are two associated problems. First, to be effective, soaking must be carried out for several hours. Second, the disinfecting solutions currently in use are irritating to the eyes of a high percentage of the users, even on a single exposure. For those users, this irritation is difficult to avoid because the disinfecting solution permeates the lenses and, therefore, is not effectively removed by rinsing the lenses in saline.

The second method of disinfection is by heating the lenses, typically in a commercially available heating unit. This is the most effective and reliable method and does not expose the user to chemical disinfecting agents. One disadvantage of heat disinfection is that protein on the surfaces of the lenses is denatured by the heat treatment and deposited on the surfaces of the lenses. Such deposited protein is not as easily removed by subsequent protease treatment, as would be the case if the protein were not deposited. In time, the incompletely removed protein may contribute to discomfort and shorten the lifetime of the lenses.

The present invention overcomes some of the problems in the previous practices by providing an effective procedure for removing protein from the surfaces of soft contact lenses during heat disinfection of the lens. The method is simple, safe, and effective.

An object of the invention is to provide a method of treating contact lenses which does not require the disinfection and protease treatment being performed in separate steps.

Another object is to provide a method of treating soft contact lenses with a heat stable protease which does not require additives for stabilization; this in turn will avoid a possible cause of eye irritation.

Still another object of the present invention is to provide a method of removing protein from contact lenses in a shorter period of time.

Still another object is to provide a method of treating contact lenses which will increase daily comfort and longevity of the lenses.

These and still further objects will become apparent hereinafter.

The foregoing objects are achieved, generally, in a method of treating soft contact lenses that comprises: immersing the lenses in a saline solution containing a heat stable protease; heating the saline/protease solution and the lenses therein to achieve disinfection; washing the lenses with a detergent solution to remove particulate matter, incompletely digested protein and protease; and rinsing the lenses in a further saline solution to remove detergent and any remaining residue.

The invention is hereinafter discussed with reference to the accompanying drawing in which:

FIGS. 1–5 are xerographic reproductions of five photographs which show electrophoresis gels in which lysozyme appears as a dark band.

DETAILED DESCRIPTION OF THE INVENTION

As discussed above, the previous practices of treating soft contact lenses have numerous pitfalls that are overcome by the present invention. According to the present teaching, the soft contact lenses are immersed in a saline solution containing a heat stable protease (saline/protease solution), the lenses and solution are heated in a commercially available heating unit to the desired temperature to achieve disinfection, the lenses are washed with a detergent (e.g., "Daily Cleaner") to remove particulate matter, incompletely digested protein and protease, and then the lenses are rinsed with saline to remove detergent and any remaining residue.

Similarly, another method of treating contact lenses in accordance with the present teaching includes all the steps of the above method, with the modification that the detergent (e.g., "Daily Cleaner") is added to the solution of saline and heat stable protease. (Such detergents include phosphate-based detergents, e.g., U.S. Pat. No. 4,395,346, and silicon-based detergents, e.g., U.S. Pat. No. 4,126,587.) Together, these are heated with the lenses to the appropriate disinfecting temperature for the proper length of time.

The saline solution into which the lenses are submerged consists of isotonic saline. The properties of the ideal protease are set forth below. The protease chosen as the example is thermolysin.

Thermolysin is stable at physiologic pH in isotonic saline, is active at disinfection temperatures (78°–80° C.), and is relatively inactive at room and body temperatures. Thus, solutions in which thermolysin would be dissolved for use with lenses would not irritate the eyes or damage the lenses if trace amounts remained after rinsing the lenses with saline.

Thermophilic proteases, as a group, and thermolysin in particular, are less likely to be irritating to the eye than currently used proteases. Currently used proteases require sulfhydryl additives for stabilization to perform their functions. For some users of soft contact lenses this chemical additive may irritate their eyes.

Furthermore, thermolysin has broad specificity in the protein types which it is capable of hydrolyzing. In general, thermolysin hydrolyzes peptide bonds of hydrophobic amino acids having bulky side chains, such as alanine, isoleucine, leucine, methionine, phenylalanine and valine. In addition, with longer reaction times and at higher protease to substrate ratios, thermolysin will also hydrolyze the peptide bonds of tyrosine, glycine, threonine, and serine. As a result, thermolysin is not likely to form insoluble, partial degradation products which in turn are further denatured by the heat treatment and deposited on the lens surface from which they are not easily removed by subsequent protease treatment. On a long-term basis there should be less intractable protein deposit formed and the lenses will be more comfortable to the user.

The protease can be provided in the form of a tablet or a powder which can be added to a lens case along with a prescribed amount of saline. The tablet is dissolved by shaking. The resulting saline/protease solution is heated to a temperature sufficient to achieve disinfection (78° C.) by placing the lens case in a commercially available heating unit. The saline/protease solution is removed and the subsequent washing and rinsing steps are performed.

It is noted above that the present method of treating soft contact lenses can be heated in a commercially available heating unit to the desire temperature, that temperature typically is at about 78° C. and for about ten minutes according to the May 1983 "Contact Lens Product Guidelines" of the Food and Drug Administration (FDA) for Class III contact lenses. Experiments by the present inventor are discussed herein. A range of temperatures from about 70° C. to 85° C. may be used, it being noted that disinfection occurs more quickly at the higher temperatures. Tests by the inventor, as noted, show 78° C. to be a useful temperature. The time for the present process to effectively degrade lysozyme is well within the ten minutes in the FDA Guidelines.

All of these photographs show electrophoresis gels in which lysozyme appears as a dark band. The electrophoresis gels separate lysozyme from its degradation products on the basis of size. As lysozyme is degraded to smaller products, the latter migrate faster on the gel than does lysozyme. When lysozyme is completely degraded, the breakdown products are so small that they migrate off the bottom of the gel, and thus, seem to "disappear."

The results of the first group of experiments are shown in the photographs labeled A, B, C, and D (i.e., FIGS. 1, 2, 3, and 4, respectively). The electrophoresis gel shown in photograph A (i.e., FIG. 1) shows that thermolysin degrades lysozyme at 78° C. in 0.9 percent saline and in 0.9 percent saline containing 10 percent "Daily Cleaner" ("Daily Cleaner" is a trademark designation of a detergent marketed by Bausch and Lomb).

Figure 1:
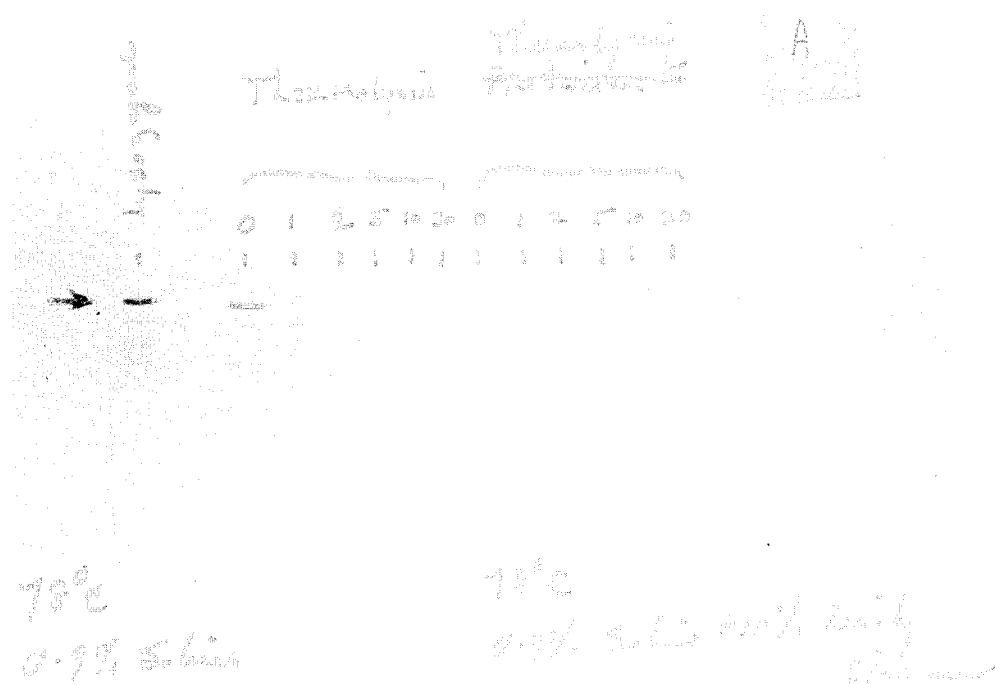
FIGS. 1–5 show results from two groups of experiments showing that thermolysin and proteinase K, two heat stable proteases, degrade lysozyme, the protein which is deposited on soft contact lenses from the user's eye. The experiments were conducted at 78° C. The results of these experiments are in the form of five glossy photographs labeled A, B, C, D, and E which are FIGS. 1–5, respectively, in the accompanying drawing.
Figure 2:
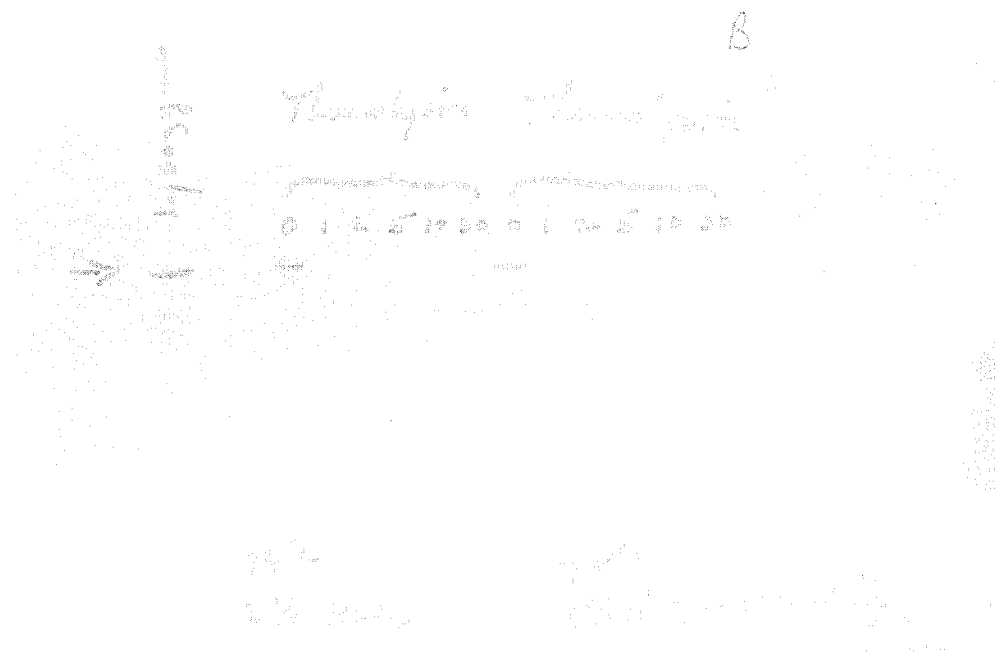

The left lane in FIG. 1 shows lysozyme which has not been treated with protease. The migration position of lysozyme is indicated by the arrow on the left. The following six lanes show samples in which lysozyme has been incubated with thermolysin in 0.9 percent saline for 0, 1, 2, 5, 10, and 30 minutes at 78° C. Further details of the experimental conditions are described below (p. 11). The sample incubated for "0" minutes establishes that the procedure used to "stop" the lysozyme treatment, described below, is effective. The following lanes, marked 1, 2, 5, 10, and 30 show that thermolysin completely degrades lysozyme, as evidenced by the disappearance of the lysozyme from the electrophoresis gel, in time periods even as short as one minute.

The last six lanes in photograph A (i.e., FIG. 1) show that thermolysin also completely degrades lysozyme in the presence of 0.9 percent saline containing 10 percent "Daily Cleaner." Again the degradation is complete in 1 minute.

The electrophoresis gel shown in photograph B (i.e., FIG. 2) shows that thermolysin degrades lysozyme in the presence of 3 percent hydrogen peroxide, and in the presence of 3 percent hydrogen peroxide plus 10 percent "Daily Cleaner." Again, the lane on the left shows lysozyme which has not been treated with thermolysin. The following six lanes show that thermolysin degrades lysozyme when incubated in the presence of 3 percent hydrogen peroxide for 1, 2, 5, 10, and 30 minutes at 78° C. In these six lanes it can be seen that the degradation of lysozyme by thermolysin is extensive, but not complete, as evidenced by the fact that at all of the incubation times (1, 2, 5, 10, and 30 minutes) the thermolysin has been degraded, but a partial degradation product can be seen in these lanes.

The last six lanes in photograph B (i.e., FIG. 2) show that thermolysin degrades lysozyme when incubated for 1, 2, 5, 10, and 30 minutes at 78° C. in 3 percent hydrogen peroxide containing 10 percent "Daily Cleaner." Again, note that the "0" minutes sample shows that the "stop" procedure is effective, in that lysozyme remains undegraded. When thermolysin is then added, the degradation is complete in 1 minute. Also, note that in the presence of 3 percent hydrogen peroxide plus "Daily Cleaner" there is no accumulation of partial degradation products.

Figure 3:
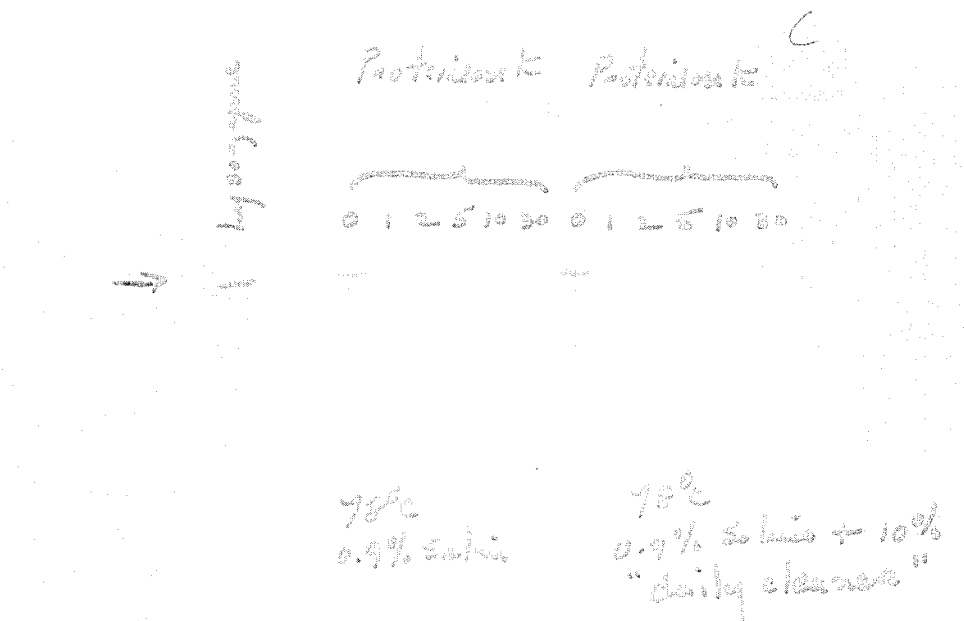
Figure 4:
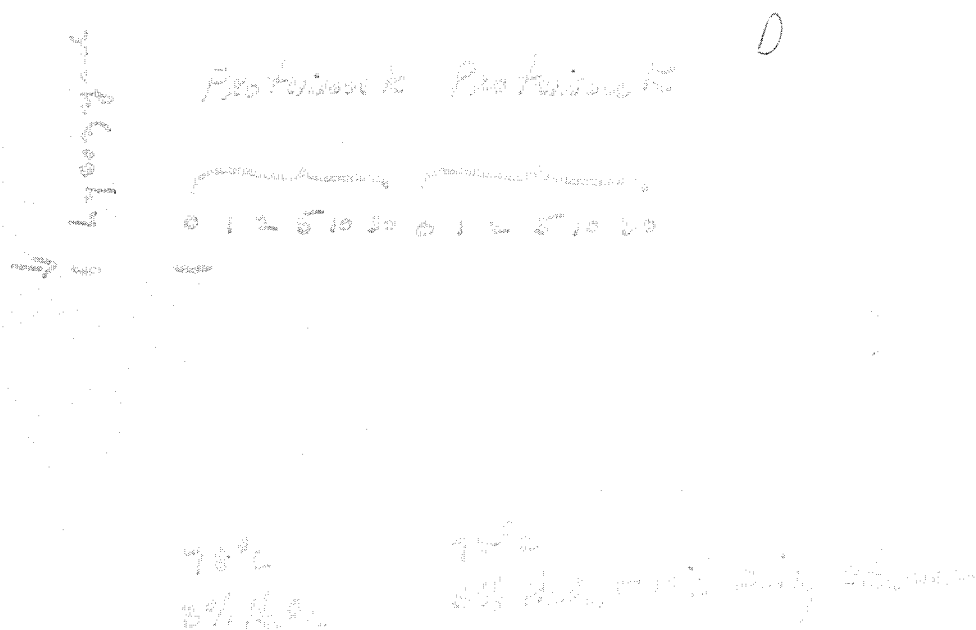

The electrophoresis gel shown in photograph C (i.e., FIG. 3) shows that proteinase K, a second example of a thermostable protease, also effectively degrades lysozyme at 78° C., in this instance in the presence of 0.9 percent saline and in the presence of 0.9 percent saline plus 10 percent "Daily Cleaner." The lane on the left shows lysozyme without exposure to protease. The following six lanes show that proteinase K degrades lysozyme when incubated for 1, 2, 5, 10, and 30 minutes, and again the degradation is complete in 1 minute. The lane marked "0" shows that the "stop" procedure is again effective with proteinase K. The last six lanes in photograph C, FIG. 3, show that proteinase K degrades lysozyme when incubated at 78° C. in the presence of 0.9 percent saline plus 10 percent "Daily Cleaner."

The electrophoresis gel shown in photograph D (i.e., FIG. 4) shows that proteinase K degrades lysozyme in the presence of 3 percent hydrogen and in the presence of 3 percent hydrogen peroxide plus 10 percent "Daily Cleaner." The lane on the left shows lysozyme without exposure to protease. The following six lanes show that proteinase K completely degrades lysozyme when incubated in the presence of 3 percent hydrogen peroxide, and the degradation is complete in 1 minute. The last six lanes show the effectiveness of proteinase K on lysozyme degradation in the presence of 3 percent hydrogen peroxide plus 10 percent "Daily Cleaner." In this instance the "0" time sample shows that the "stop" procedure is not completely effective, and that there is apparently some degradation of the lysozyme by the proteinase K after "stopping" the reaction.

The conditions of the experiments described in photographs A, B, C, and D (i.e., FIGS. 1, 2, 3, and 4, respectively) were as follows. Lysozyme was dissolved at a concentration of 10 mg/ml in either 0.9 percent saline, 0.9 percent saline plus 10 percent "Daily Cleaner," 3 percent hydrogen peroxide, or 3 percent hydrogen peroxide plus "Daily Cleaner." The resulting 2 ml solution of lysozyme was then incubated in a glass tube immersed in a heated water bath until the temperature of the lysozyme solution reached 78° C. The temperature of the bath was approximately 82° C.; the temperature of the lysozyme solution in the tube was measured with a glass thermometer and determined to be 78° C. A $\mu$l aliquot of either 50 mg/ml thermolysin or 50 mg/ml proteinase K, dissolved in the same reaction solution as the lysozyme, was then added to the 2 ml solution of lysozyme to obtain a reaction mixture containing 1 mg/ml thermolysin or 1 mg/ml proteinase K and 10 mg/ml lysozyme.

After adding the protease, a 50 $\mu$l aliquot was immediately withdrawn as a "0" time sample, and subsequent timed samples were withdrawn at 1, 2, 5, 10, and 30 minutes. All of these samples were "stopped" by transferring the 50 $\mu$l aliquots to 450 $\mu$l of 5 percent sodium dodecyl sulfate, previously heated to 95° C. The "stopped" samples, in 5 percent sodium dodecyl sulfate were then analyzed by electrophoresis on polyacrylamide electrophoresis gels in the presence of sodium dodecyl sulfate. The electrophoresis gels were formed from a 15 to 20 percent gradient of acrylamide. The electrophoresis gels were stained with Coomasie blue, to detect protein, and the stained gels were photographed.

The above experiments were conducted for varying periods of time, with constant amounts of protease. In the experiment which follows, differing amounts of thermolysin and proteinase K were tested for 1 and 5 minutes.

Figure 5:
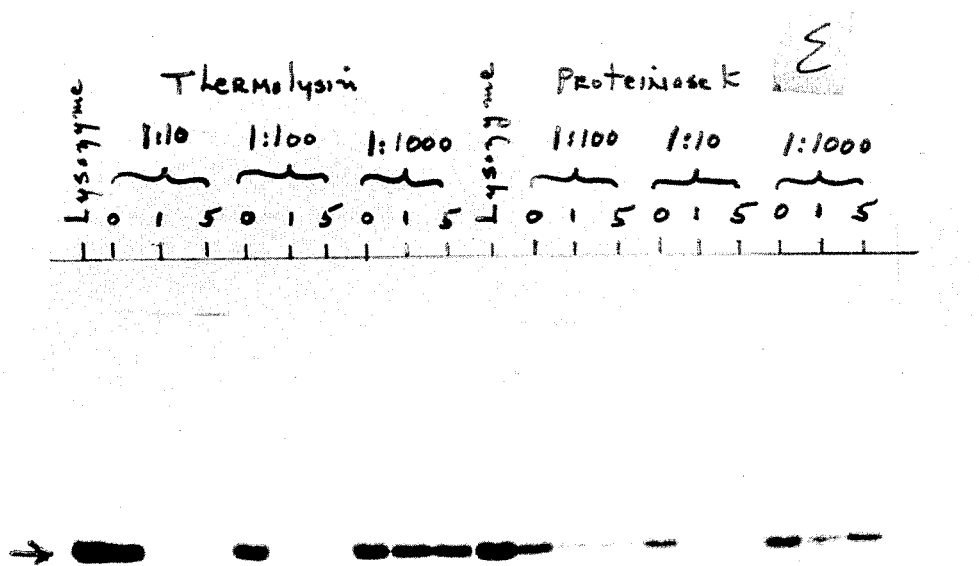

The photograph labeled E (i.e., FIG. 5) shows the results of this second experiment, in which the relative efficacy of varying amounts of thermolysin and proteinase K were compared in regard to their ability to degrade lysozyme at 78° C. in 0.9 percent saline. In this experiment thermolysin or proteinase K was incubated with lysozyme for 0, 1, and 5 minutes, and the amount of protease was varied so that the ratios of protease to lysozyme were 1:10, 1:100, and 1:1000.

The left lane of the electrophoresis gel shows lysozyme, which was not exposed to protease. The next three lanes show lysozyme after exposure to thermolysin at a 1:10 ratio of thermolysin:lysozyme for 0, 1, and 5 minutes. The result is that after only 1 minute thermolysin at a 1:10 ratio has completely degraded the lysozyme. The 0 minutes sample shows that lysozyme is not degraded after the "stop" procedure. The next three lanes show an analogous result, except the ratio of thermolysin to lysozyme was 1:100. In this instance the degradation of lysozyme is more than 90 percent complete in 1 and 5 minutes, as evidenced by the fact that only a trace of the original lysozyme is visible in the 1 and 5 minute lanes. The next three lanes show the result when the ratio of thermolysin to lysozyme is so low (1:1000) that there is virtually no degradation of the lysozyme.

The lane in the middle of the gel again shows lysozyme which was not incubated with protease. The following nine lanes show the degradation of lysozyme by proteinase K at ratios of 1:100, 1:10, and 1:1000. At ratios of 1:10 the proteinase K also completely degrades the lysozyme after only 1 minute of incubation at 78° C. At a ratio of proteinase K to lysozyme of 1:100 there is partial, but incomplete degradation of the lysozyme. By comparing the 1 and 5 minute lanes of the 1:100 proteinase K sample with the 1:100 thermolysin sample it can be seen that thermolysin is somewhat more effective at degrading lysozyme. The last three lanes show that at a ratio of 1:1000 there is very little degradation of the lysozyme by the proteinase K.

The conditions of the experiments shown in photograph E (i.e., FIG. 5) were as follows. Lysozyme was dissolved at 10 mg/ml in 1 ml of 0.9 percent saline. A 50 $\mu$l aliquot of a stock solution of either thermolysin or proteinase K was then added to obtain a concentration of thermolysin or proteinase K of 1 mg/ml, 100 $\mu$g/ml, or 10 $\mu$g per ml, equivalent to a 1:10, 1:100, or 1:1000 ratio of thermolysin:lysozyme or proteinase K:lysozyme.

These results demonstrate the claim that thermostable proteases, as illustrated here by thermolysin and proteinase K, will degrade lysozyme, the protein which is deposited on the surface of soft contact lenses, when the protease is incubated with the lysozyme at elevated temperatures (78° C.) as required for disinfection. Furthermore, the results of the first series of experiments show that both thermolysin and proteinase K are active in the presence of the detergent "Daily Cleaner." In addition, the first series of experiments also show that thermolysin and proteinase K are active in the presence of 3 percent hydrogen peroxide, which is a commonly used agent for disinfecting soft contact lenses.

A heat stable protease as is known in this art and as is the term used herein denotes a protease that is stable and active at temperatures higher than 70° C. One such heat stable protease is thermolysin. Reference may be had to pages 642–650 of "Proteolytic Enzymes," Perlmann et al. (1970) Methods in Enzymology, vol. XIX, Academic Press, which shows clearly that thermolysin is well identified chemically. Another thermal stable protease is proteinase K which, like thermolysin, acts to degrade lysozyme, the protease acting as a catalyst in the process.

Further modifications of the invention herein described will occur to persons skilled in the art and all such modifications are deemed to be within the scope of the invention as defined by the appended claims.

What is claimed is:

1. A method of cleaning and disinfecting soft contact lenses, comprising:
   immersing the lenses in a $H_2O_2$ solution comprising effective amounts of a thermophilic protease which is stable and active at a temperature higher than about 70° C., said protease having broad hydrolytic specificity such that it is able to hydrolyze and substantially completely remove proteins from the lenses at said temperature; and heating the lenses and the solution to a temperature higher than about 70° C. and maintaining said temperature for a period of time effective to achieve the simultaneous disinfection of the lenses and the substantially complete removal of the protein.

2. The method of claim 1, further comprising washing the lenses with a detergent solution to remove particulate matter, incompletely digested protein and protease; and rinsing the lenses.

3. The method of claim 1, wherein the saline solution is an isotonic solution; and the $H_2O_2$ solution is an about three percent $H_2O_2$ solution.

4. The method of claim 1, wherein the disinfecting temperature is about 78° C. to 80° C.

5. The method of claim 1, wherein the heat-stable protease is thermolysin.

6. The method of claim 1, wherein the heat-stable protease is proteinase K.

7. The method of claim 1, wherein the heat-stable protease is free of sulfhydryl groups.

8. A method of cleaning and disinfecting soft contact lenses, comprising immersing the lenses in a $H_2O_2$ solution comprising a thermophilic protease which is stable and active at a temperature higher than about 70° C. for a period of time effective to disinfect and clean the lenses, said protease being capable of hydrolyzing and removing protein from the lenses; and thereafter removing any remaining residue from the said lenses.

9. The method of claim 8, wherein the temperature is about 78 and 80° C.

10. A method of cleaning and disinfecting a soft contact lens, comprising subjecting the soft contact lens to a mixture comprising a hydrophilic protease which is stable and active at a temperature greater than about 70° C. and comprises substantially no sulfhydryl groups, and $H_2O_2$, thereby removing protein from the soft contact lens, and disinfecting the soft contact lens.

* * * * *

UNITED STATES PATENT AND TRADEMARK OFFICE
CERTIFICATE OF CORRECTION

PATENT NO. : 4,832,754
DATED : May 23, 1989
INVENTOR(S) : Bernard L. TRUMPOWER

It is certified that error appears in the above-identified patent and that said Letters Patent is hereby corrected as shown below:

IN THE ABSTRACT line 3, after "protease" insert --in the presence of $H_2O_2$.--.

IN THE CLAIMS

Column 8, line 18, change "hydrophilic" to --thermophilic--.

Signed and Sealed this

Twenty-seventh Day of November, 1990

Attest:

HARRY F. MANBECK, JR.

*Attesting Officer*      *Commissioner of Patents and Trademarks*